US011628197B2

(12) United States Patent
Chitre et al.

(10) Patent No.: US 11,628,197 B2
(45) Date of Patent: Apr. 18, 2023

(54) METHODS AND COMPOUNDS FOR TREATING EFFECTS OF COVID-19 DISEASE

(71) Applicant: Bioved Pharmaceuticals, Inc., San Jose, CA (US)

(72) Inventors: Deepa Chitre, Los Gatos, CA (US); Debendranath Dey, Fremont, CA (US); Satej R Nadkarni, San Jose, CA (US)

(73) Assignee: Bioved Pharmaceuticals, Inc, San Jose, CA (US)

( * ) Notice: Subject to any disclaimer, the term of this patent is extended or adjusted under 35 U.S.C. 154(b) by 62 days.

(21) Appl. No.: 17/306,937

(22) Filed: May 3, 2021

(65) Prior Publication Data

US 2021/0338765 A1    Nov. 4, 2021

Related U.S. Application Data

(60) Provisional application No. 63/019,412, filed on May 3, 2020.

(51) Int. Cl.

| | |
|---|---|
| *A61K 36/9066* | (2006.01) |
| *A61K 36/324* | (2006.01) |
| *A61K 31/25* | (2006.01) |
| *A61K 45/06* | (2006.01) |
| *A61K 36/268* | (2006.01) |
| *A61K 31/375* | (2006.01) |
| *A61K 31/315* | (2006.01) |
| *A61K 31/197* | (2006.01) |

(52) U.S. Cl.
CPC ........ *A61K 36/9066* (2013.01); *A61K 31/197* (2013.01); *A61K 31/25* (2013.01); *A61K 31/315* (2013.01); *A61K 31/375* (2013.01); *A61K 36/268* (2013.01); *A61K 36/324* (2013.01); *A61K 45/06* (2013.01)

(58) Field of Classification Search
None
See application file for complete search history.

(56) References Cited

U.S. PATENT DOCUMENTS

2017/0007625 A1*   1/2017   Chitre ............... A61K 36/9068

OTHER PUBLICATIONS

Jose, R.C., Manuel, A., COVID-19 cytokine storm: the interplay between inflammation and coagulation, The Lancet Respiratory Medicine, Published Online Apr. 27, 2020 https://doi.org/10.1016/S2213-2600(20)30216-2 (Year: 2020).*
Padmawar & Bhadoriya, Glycol And Glycerin: Pivotal Role in Herbal Industry as Solvent/Co-Solvent, World Journal of Pharmaceutical and Medical Research, wjpmr, 2018,4(5), 153-155 (Year: 2018).*

* cited by examiner

*Primary Examiner* — H. Sarah Park
(74) *Attorney, Agent, or Firm* — Farrell Patent Law PC; Mark Farrell

(57) ABSTRACT

Methods and compounds for preventing and arresting COVID-19 morbidity and mortality, via inhibition of Interleukin-6, TNF-alpha, and other cytokines, and via reduction of C-reactive proteins are provided. Analyses of patients with COVID-19 complicated by ARDS, for example, show highly activated cytotoxic T-cells, resulting from hyperactivation of the immune system. A significant surge of Interleukin-6 (IL-6), TNF-α, and other cytokines are thought to be mediators of this enhanced T-cell activity, and runaway inflammation that are dangerous or fatal to the patient. Example oral formulations dubbed BV-4051 and Artovid-20 provide prophylaxis and treatment of these conditions caused by COVID-19 disease. The example formulations contain plant extracts boosting the human immune system and targeting the detrimental effects of the SARS-CoV-2 virus in its various strains.

9 Claims, 12 Drawing Sheets

800

```
┌─────────────────────────────────────────────┐
│ Obtain an Ashwagandha (Withania somnifera)  │
│ extract from a first hydro glycolic         │
│ extraction process                          │
│ 802                                         │
└─────────────────────────────────────────────┘
                      ↓
┌─────────────────────────────────────────────┐
│ Obtain a Shallaki (Boswellia serrata)       │
│ extract from a second hydro glycolic        │
│ extraction process                          │
│ 804                                         │
└─────────────────────────────────────────────┘
                      ↓
┌─────────────────────────────────────────────┐
│ Obtain a Ginger (Zingiber officinale)       │
│ extract from a third hydro glycolic         │
│ extraction process                          │
│ 806                                         │
└─────────────────────────────────────────────┘
                      ↓
┌─────────────────────────────────────────────┐
│ Obtain a Turmeric extract (Curcuma longa,   │
│ Family Zingiberaceae) from a fourth hydro   │
│ glycolic extraction process                 │
│ 808                                         │
└─────────────────────────────────────────────┘
                      ↓
┌─────────────────────────────────────────────┐
│ Mix the Ashwagandha, the Shallaki, the      │
│ Ginger, and the Turmeric into a compound    │
│ comprising by weight, approximately 5.00    │
│ parts of the Ashwagandha, 5.00 parts of the │
│ Shallaki, 1.33 parts of the Ginger, and     │
│ 1.00 parts of theTurmeric                   │
│ 810                                         │
└─────────────────────────────────────────────┘
                      ↓
┌─────────────────────────────────────────────┐
│ Administer the compound orally to a         │
│ Covid-19 patient                            │
│ 812                                         │
└─────────────────────────────────────────────┘
```

*Fig.8*

Table 14.1.1.1 Subject Disposition - All Subject Data

|  | BV-4051<br>(N=89)<br>n(%) | Placebo<br>(N=87)<br>n(%) | Total<br>(N=176)<br>n(%) |
|---|---|---|---|
| Number of Randomized Subjects | 89 (100) | 87 (100) | 176 (100) |
| Number of subjects in Safety population | 89 (100) | 87 (100) | 176 (100) |
| Number of subjects in ITT population | 89 (100) | 87 (100) | 176 (100) |
| Number of subjects in PP population | 89 (100) | 86 (98.9) | 175 (99.4) |
| Number of subjects who completed the study | 89 (100) | 87 (100) | 176 (100) |
| Number of subjects withdrawal/ discontinuations | 0 | 0 | 0 |

Abbreviations: N = number of subjects in specified treatment group; n = number of subjects in specified category
Note 1: Percentages are based on the number of subjects in the specified treatment group.
Reference listing 16.2.1.2

*Fig.9*

Table 14.1.2.1 Demographic Characteristics - Safety Population

| Characteristic (Unit) | Statistics | BV-4051 (N=82) | Placebo (N=76) | Total (N=158) |
|---|---|---|---|---|
| Gender | | | | |
| Male | n (%) | 55 (67.1) | 51 (67.1) | 106 (67.1) |
| Female | n (%) | 26 (31.7) | 22 (28.9) | 48 (30.4) |
| | | | | |
| Age (Years) | n | 81 | 73 | 154 |
| | Mean (SD) | 43.4 (11.90) | 42.3 (11.22) | 42.8 (11.56) |
| | Median | 43.0 | 41.0 | 42.5 |
| | Min, Max | 20, 65 | 20, 65 | 20, 65 |
| | | | | |
| Race | | | | |
| White | n (%) | 0 | 0 | 0 |
| Black | n (%) | 0 | 0 | 0 |
| Asian | n (%) | 75 (91.5) | 69 (90.8) | 144 (91.1) |
| Native American | n (%) | 0 | 0 | 0 |
| Other | n (%) | 6 (7.3) | 4 (5.3) | 10 (6.3) |

Abbreviations: N = number of subjects in specified treatment group; n = number of subjects in specified category
Note 1: Percentages are based on the number of subjects in the specified treatment group.
Reference Listing 16.2.4.1

Fig.10

Table 14.3.1.1 Primary Efficacy Analysis - ITT1 Population

| | Statistics | BV-4051 (N=89) | Placebo (N=87) |
|---|---|---|---|
| Reduction in Duration of Illness (in Days) | n | 83 | 86 |
| | Mean(SD) | 7.9(3.33) | 8.8(3.57) |
| | Median | 9.0 | 10.0 |
| | Min,Max | 1,14 | 1,13 |
| | Median Diff (95% CI)* | -1(-2.00 - 0.00) | |
| | p value* | 0.038 | |

Abbreviations: N = number of subjects in specified treatment group, n = number of subjects in specified category.
Note 1: *Median difference, 95% CI and p value is calculated for non-parametric Mann-Whitney U-Test
Note 2: Duration of illness = the length of time to alleviation of all symptoms including fever and other symptoms including breathing difficulty, nasal congestion, sore throat, cough, headache, body ache, fatigue, chills or sweats, diarrhea, vomiting, taste and smell disorders.
Reference Listing 16.2.7.2

Fig.11

Table 14.2.1.2 Primary Efficacy Analysis - PP Population

| | Statistics | BV-4051 (N=89) | Placebo (N=86) |
|---|---|---|---|
| Reduction in Duration of Illness (in Days) | n | 83 | 85 |
| | Mean(SD) | 7.9(3.33) | 8.9(3.51) |
| | Median | 9.0 | 10.0 |
| | Min,Max | 1,14 | 1,13 |
| | Median Diff (95% CI)* | -1( -2.00 ~ 0.00 ) | |
| | p-value* | 0.027 | |

Abbreviations: N = number of subjects in specified treatment group; n = number of subjects in specified category.
Note 1: *Median difference, 95% CI and p value is calculated for non-parametric Mann-Whitney U-Test
Note 2: Duration of illness = the length of time to alleviation of all symptoms including fever and other symptoms including breathing difficulty, nasal congestion, sore throat, cough, headache, body ache, fatigue, chills or sweats, diarrhea, vomiting, taste and smell disorders.
Reference Listing 16.2.7.2

*Fig.12*

METHODS AND COMPOUNDS FOR TREATING EFFECTS OF COVID-19 DISEASE

RELATED APPLICATIONS

This nonprovisional patent application claims the benefit of priority to U.S. Provisional Patent Application No. 63/019,412 to Chitre et al., filed May 3, 2020 and incorporated by reference herein in its entirety.

BACKGROUND

To date, COVID-19 disease has affected only a comparatively small percentage of the worldwide population, with severity of its impact being highly variable between countries. It is estimated that within the next few months of this writing, more than 55% of the world population will be positive for COVID-19 disease. As many as 75% of positive cases can be asymptomatic, while the asymptomatic carriers continue spreading the virus. In a majority of cases, signs and symptoms of COVID-19 disease are mild to moderate and resolve. However, in vulnerable populations the disease manifests as an overwhelming and potentially fatal condition. Besides advanced age, predisposing conditions such as hypertension, diabetes, congestive heart failure, obesity, cancers, and immunosuppression, for various reasons, lead to increased intensity of the disease and a poor prognosis. The COVID-19 disease appears to produce runaway inflammation, direct destruction of lung cells involved in gas exchange and their impaired regeneration, and accelerated lung scarring in those seriously afflicted.

Some vaccines have been developed for COVID-19 disease, but have to be stored in ultra cold temperatures, for example between −80° C. and −60° C. Common side effects of these vaccines are chills, headache, pain, tiredness, and/or redness and swelling at the injection site but the vaccines are rarely found to trigger anaphylaxis. A 15-30 minute wait time is recommended by CDC for monitoring after administration of the vaccines. The long-term efficacies of the vaccines are currently unknown with the virus continuing to mutate into new stains among infected populations.

In addition to the vaccines, the U.S. FDA has currently issued Emergency Use Authorization for Remdesivir, a broad-spectrum antiviral medication (Gilead Sciences, Foster City, Calif.). Convalescent plasma therapy has also been conditionally approved for treating some Covid-19 patients.

Evidence suggests that infection with COVID-19 disease may predispose individuals to both venous and arterial thromboembolism due to excessive inflammation, hypoxia, immobilization and diffuse intravascular coagulation. This is estimated to happen in up to 31% of patients, hence it is important to prevent these by giving adequate preventive and prophylactic treatment.

Autopsy analyses of patients with COVID-19 disease complicated by Acute Respiratory Distress Syndrome (ARDS) show highly activated cytotoxic T-cells, resulting from hyperactivation of the immune system. A significant surge of Interleukin-6 (IL-6), Tumor Necrosis Factor-alpha (TNF-α), and other cytokines are thought to be the mediators of this enhanced T-cell activity.

BRIEF DESCRIPTION OF THE DRAWINGS

FIG. 8 is a flow diagram of an example method of neutralizing a COVID-19 disease-specific pro-inflammatory cytokine, in a Covid-19 patient.

FIG. 9 is a table showing subject disposition for the Phase III Clinical Trial entitled, "Multi-center, Randomized, Double-Blind, Placebo-Controlled Phase III Clinical Study to assess the Safety and Efficacy of BV-4051 Tablets combined with the Current Standard of Care and its impact on Inflammatory Biomarkers in Subjects with Uncomplicated Moderate SARS-CoV-2 infections (COVID-19)."

FIG. 10 is a table showing demographic characteristics for the Phase III Clinical Trial entitled, "Multi-center, Randomized, Double-Blind, Placebo-Controlled Phase III Clinical Study to assess the Safety and Efficacy of BV-4051 Tablets combined with the Current Standard of Care and its impact on Inflammatory Biomarkers in Subjects with Uncomplicated Moderate SARS-CoV-2 infections (COVID-19)."

FIG. 11 is a table showing a primary efficacy analysis, ITTI Population, for the Phase III Clinical Trial entitled, "Multi-center, Randomized, Double-Blind, Placebo-Controlled Phase III Clinical Study to assess the Safety and Efficacy of BV-4051 Tablets combined with the Current Standard of Care and its impact on Inflammatory Biomarkers in Subjects with Uncomplicated Moderate SARS-CoV-2 infections (COVID-19)."

FIG. 12 is a table showing a primary efficacy analysis, PP Population, for the Phase III Clinical Trial entitled, "Multi-center, Randomized, Double-Blind, Placebo-Controlled Phase III Clinical Study to assess the Safety and Efficacy of BV-4051 Tablets combined with the Current Standard of Care and its impact on Inflammatory Biomarkers in Subjects with Uncomplicated Moderate SARS-CoV-2 infections (COVID-19)."

DETAILED DESCRIPTION

Overview

This application describes methods and compounds for preventing and arresting COVID-19 morbidity and mortality, via Inhibition of Interleukin-6, TNF-alpha, and other cytokines, and via reduction of C-reactive proteins.

Described herein are use methods, preparations for prevention and treatment of conditions caused by the COVID-19 viral disease, preparations for boosting the human body's immune system, and methods and preparations for preventing and counteracting the cytokine storm as seen in infections with the SARS-CoV-2 virus and other viral infections. An example formulation consists of a synergistic and specialized combination of certain plants, for example, in tablet, capsule, or liquid dosage form for oral administration.

In an implementation, a formulation referred to herein as BV-4051 can inhibit IL-6 and TNF-α in COVID-19 disease.

A Phase III randomized, double-blind, placebo-controlled clinical study in ~176 subjects of moderate Sars-COV2 infection conducted recently is presented as supportive evidence later in this application. In one implementation, a formulation of BV-4051 is referred to as Artovid-20.

Example Clinical Circumstances

Current reports describe the immunological profile of patients critically ill with COVID-19 disease. Immune hyperactivation is precipitated by a surge of critical immune mediators, including Interleukin-6 (IL-6), that lead to respiratory failure, shock, and multi-organ dysfunction. It is likely that a severe storm of many proinflammatory cytokines simultaneously create the havoc and fatality in this disease. Various previously known agents against SARS, Ebola and MERS targets, are being researched by in-vitro and computational analytic approaches. Agents such as hydroxycholoroquine and chloroquine have failed to produce desired therapeutic effects after clinical testing in US Veterans Administration hospitals, as well as in France, China and Brazil. Similarly, promising antiviral treatments such as Remdesivir have failed to make the impact expected in early studies, but are still prescribed for want of more definitive therapies.

A humanized monoclonal antibody (tocilizumab) targeting IL-6 receptors and blocking downstream pro-inflammatory effects of cytokines have been promoted for COVID-19 disease without consideration of its side effects and high cost. Biologics have been tried, to block TNF-α. The biologics include etanercept, infliximab, abatacept, and adalumimab, which are a primary treatment modality in diseases mediated by TNF-α. The biologics are being tested for treatment of COVID-19 disease in aggressive studies. However, the biologic agents can have serious adverse effects such as tuberculosis reactivation and decrease of defense against overwhelming infection, as well as predisposition to development of lymphoma, or fatal malignancies. Cost is also high and prohibitive for large populations.

Given the above challenges with respect to prevention and treatment regimens currently being considered for COVID-19 disease, and in light of an alarming increase in number of cases worldwide, even after two doses of the vaccines have been distributed to millions, the need for an option that is safe, cost-effective, easy to store, and easy to administer, e.g., orally in either solid or liquid dosage form, may be a suitable therapy or adjunct for the global COVID-19 pandemic.

Example Formulations

In an implementation, an example preparation alleviates a cytokine storm consequence of COVID-19 disease, and/or reduces the viral load. A formulation referred to as BV-4051 comprises specialized extracts of medicinal plants, including Ashwagandha (*Withania somnifera*, Family Solanaceae), Shallaki (*Boswellia serrata*, Family Burseraceae), Ginger (*Zingiber officinale*, Family Zingiberaceae) and Turmeric (*Curcuma longa*, Family Zingiberaceae), for example. Combinations of these agents can address autoimmune disease conditions, which may have similar pathophysiologies to COVID-19 disease, and can provide immuno-modulatory and anti-inflammatory properties. Combinations may prevent coagulation that can lead to other severe or fatal complications.

In an example formulation, active ingredients of four types of plants are extracted, for example, by the techniques described in U.S. Pat. No. 8,808,769 to Chitre et al., entitled, "Method for Extraction of Fractions Containing Pharmacologically Active Ingredients with Less Cytotoxicity from One or More Plants," which is incorporated herein by reference in its entirety. In particular ratios, standardization, and characterization, and at a described methods of manufacture, the example formulation shows efficacy inhibiting IL-6 and TNF-α in various stages of inflammation. The example formulation may help COVID-19 patients, both in preventing the onset or the severity of symptoms, as well as to reducing the intensity of the manifestations and morbidity of the COVID-19 disease. The example formulation may work across multiple strains of the SARS-CoV-2 virus.

The example formulations may work in conjunction with the COVID-19 vaccines, and also as a prophylaxis in people who have been exposed to active COVID-19 disease, such as those who work in professions that make them more susceptible to exposure and infection with the SARS-CoV-2 virus.

Example Extraction and Preparation of BV-4051 Formulation

An example method of extraction, as described in U.S. Pat. No. 8,808,769 to Chitre et al., for example, yields bioactive compounds that may be more pharmacologically efficacious than those extracted by conventional extraction methods, due to concentration, purity, and careful preservation and non-destruction of the desired active chemical species of the selected plants.

The plant material obtained from the one or more types of plants is subjected to hydro-alcoholic extraction in presence of a water-insoluble solvent. The hydro-alcoholic extraction includes soaking the plant material in a mixture of aqueous alcohol and the water-insoluble solvent for a predetermined time. The water-insoluble solvent used in the hydro-alcoholic extraction may be one of, but not limited to, chloroform, acetone, dichloromethane and tetra-chloromethane, for example. The mixture may be occasionally stirred while plant materials are allowed to soak. The stirring may be accomplished using methods known in the art, such as laboratory or industrial stirrer/shaker, or optionally the mixture may be stirred manually by using an appropriate stirrer. In order to extract the pharmacologically active ingredients effectively, the water-insoluble solvent and the aqueous alcohol present in the mixture should penetrate the tissues and/or cells of the plant material for a specified length of time, and with the periodic agitation or stirring.

Secondary metabolites may then be dissolved in the solvent and further extracted. Soaking plant material in the mixture of the aqueous alcohol and the water-insoluble solvent results in extraction of the pharmacologically active ingredients of the one or more plants in two different phases. The two different phases may be a hydro-alcoholic phase and a water-insoluble phase. After, predetermined soaking times are over, the mixtures are filtered. The filtration may be carried out using the methods generally known and used in the art of liquid-liquid extraction. Alternatively, the filtration may be achieved using laboratory or industrial filtration procedures. As a result of filtering the mixture, a first residue and a first filtrate are obtained. The dry extract is subjected to one or more of a de-pigmentation process, a de-fatting process, and/or a detoxification process.

In an example formulation of BV-4051, the raw plant parts, such as roots of *Withania somnifera*, gum resin of *Boswellia serrata*, and roots of *Curcuma longa* and *Zingiber officinale* are each gathered individually. After washing they are minced and soaked overnight in the alcohol-water mixture, and processed as described in U.S. Pat. No. 8,808,769 to Chitre et al. The mixtures may be cleared up by a defatting agent before testing for standardization and before analytical testing by High Performance Liquid Chromatography (HPLC), High Pressure Thin Layer Liquid Chromatography (HPTLC) and Ultra-violet spectrophotometry. Once the four extracts are obtained, further manufacture to a dosage form of tablet is performed as described below. The extracts can be subjected to further development into a liquid formulation as described further below.

Example Tablet Manufacturing Process

Figure 1:
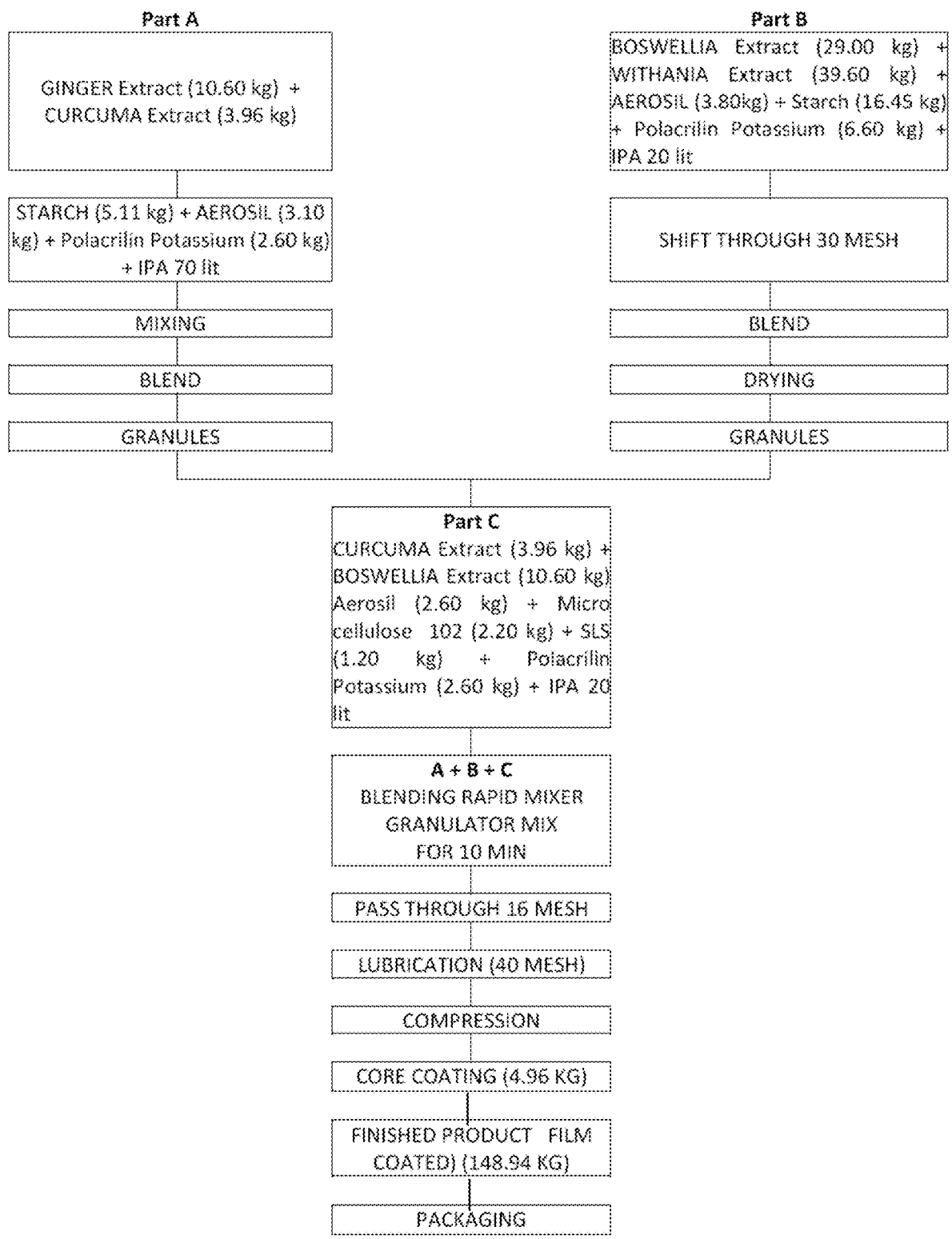
FIG. 1 is a diagram of an example process for making a batch size of approximately 220,000 tablets of an example BV-4051 formulation.

FIG. 1 shows an example process for making a batch size of approximately 220,000 tablets. Further detail, in reference to FIG. 1, is now provided:
i. Stainless steel (SS) vessels can be prepared with 316 quality stainless steel sheets.
ii. In one process, only stainless steel scoops and spatulas are used for removing the required quantity of extracts.
Step A. Granulation—Ginger and *Curcuma*
i. Weigh ginger extract (10.60 kg) and *Curcuma* extract (3.96 kg) accurately.
ii. Pass starch maize (5.11 kg) and colloidal anhydrous silica (3.10 kg) through a 40 mesh SS sieve.
iii. Mix the above ingredients together in a suitable mass mixer for 30 min with Polacrilin potassium (2.60 kg).
iv. Add the ginger extract and *Curcuma* extract and mix well.
v. Granulate material using isopropyl alcohol (IPA) (14 lit).
vi. Pass the above mixture thorough a 30 mesh sieve.
vii. Dry granulate at 45-50° C. until loss on drying (LOD) is 2-3% only.
Step B. Granulation—*Withania* and *Boswellia*
i. Weigh the *Withania* extract (39.60 kg) accurately in SS container and pass through a 16 mesh SS sieve.
ii. Weigh *Boswellia* extract (29.00 kg) accurately in powder form in SS vessel and pass through a multi-mill 2 mm screen. Collect in a suitable SS container.
iii. Mix both extracts with colloidal silicone dioxide (e.g., Aerosil) (3.80 kg), starch maize (16.45 kg) and Polacrilin potassium (6.60 kg).
iv. Granulate above material using IPA (4.5 Lit)
v. Pass the above mix thorough a 30 mesh sieve.
vi. Dry mix for 15 min.
vii. Dry granules at 45° C.-50° C. till LOD is 2-3%
Step C. Mixing of Granules
i. Mix Part A and Part B granules in a rapid mixer granulator for 10 min. Granulate with colloidal silicon dioxide (2.60 kg), *Curcuma* extract (3.96 kg), *Boswellia* extract (10.60 kg), Polacrilin potassium (2.60 kg), microcrystalline cellulose (2.20 kg) and sodium lauryl sulfate (1.20 kg) with IPA (4.5 Liters), then pass through a 40 #sieve. Add in rapid mixer granulator and blend to desired consistency.
ii. Mix for 15 min.
iii. Dry the wet mass in a fluid bed dryer (FBD) at room temperature for 20 min.
iv. Pass this mass through a multi-mill using a 12 mesh sieve to form uniform granules.
v. Dry these granules formed in a fluid bed dryer with inlet air temperature of 60-70° C. until the outlet air temperature reaches 38° C. (or till the moisture content of the granules is 2-3%).
vi. Sift the semi-dried granules through a 16 mesh sieve and mill the retention through multi-mill and cad-mill using 1.5 mm screen.
vii. Load the dried granules in a double cone blender and mix for 10 mins.
viii. Sift lubrication material through a 40 #sieve.
ix. Add lubrication material to dried granules and mix for 10 minutes.
x. Compress the tablets on a compression machine
xi. Complete film coating with clear colorcoat (4.96 kg) on Ganscota.
Step D. In-Process Quality Control Procedures
In-process testing is done at the following stages:
i. Moisture content of both the granules is checked after necessary size reduction and drying. Q.A. personnel draw the composite sample.
ii. Moisture content is determined using a Karl Fischer Titrimeter, for example. Further processing is done after getting a compliance report from Q.A. (Limit for Step A granules: 2-3%, and for Step B granules: 2-3%)
iii. Moisture content of the final blend of tablets (ready for filling) is checked by Q.A. personnel, for example.
iv. During compression of tablet, the atmospheric conditions of temperature and relative humidity are monitored every hour. Average weight of the tablets is checked every 15 minutes.

Example Liquid Formulation of BV-4051 for Elderly COVID-19 Patients

A liquid or syrup form of an example BV-4051 formulation effectively implements treatment in more vulnerable populations, such as elderly patients. For older individuals, swallowing tablets can be challenging. The formulation of a liquid dosage form of the plants, such as the four example herbs used above, that can be dosed with similar efficacy, addresses this issue. As previously mentioned, the highest death rate from COVID-19 diseased has occurred in the elderly age group, at least in one phase of the pandemic. The option of having a liquid formulation helps the ultimate delivery and patient compliance of the treatment regimen.

To generate an example liquid form, the plants are individually extracted using a hydro glycolic extraction process. Propylene glycol is used as a co-solvent, for example as a 50% mixture in water. Propylene glycol is a colorless and odorless liquid with a sweet taste. It is used in foods, beverages and in drinks as a solubilizer, fragrance enhancer and viscosity modifier, and is widely applied in mouthwash and toothpaste. The propylene glycol offers a wide range of advantages such as, biocompatibility, biodegradability, stability, hygroscopic, non-toxic and more importantly water solubility. It also possesses bacteriostatic and fungistatic properties, and can thus act as a preservative.

The plant extracts, such as extracts of the four herbs described above, are mixed, in approximately the same ratio as in the solid tablet form described above. Concentrations of the biologically active markers are documented by High Performance Liquid Chromatography (HPLC) and by Thin Layer Chromatography (TLC). This ensures that the same activity is present in the liquid form as in the oral tablets or capsules. The mixture is a clear liquid with a pleasant taste that can be easily administered to elderly or ill patients, and for ease of use in the general population.

Example Outcomes

BV-4051 Lowers IL-6 Levels—Rheumatoid Arthritis (RA) Study

A total of 182 patients were enrolled in this clinical study, of which there were 165 evaluable cases. 89 of these 165 patients were treated with an example formulation of BV-4051 while 93 patients received placebo. The mean age of study population in both the groups was 45 years, with both cohorts well matched for baseline demographics. After completion of 16 weeks of therapy and analysis of the resulting data, continuation of therapy was opted for to prolong assessment of the drug. Willing participants from the BV-4051 group were enrolled into this Open Label Phase (OLP) of the study and treatment was continued for a further period of 16 weeks. All patients were followed in an OLP for 32 weeks and for 52 weeks thereafter with a subset followed for 10 years.

Figure 2:
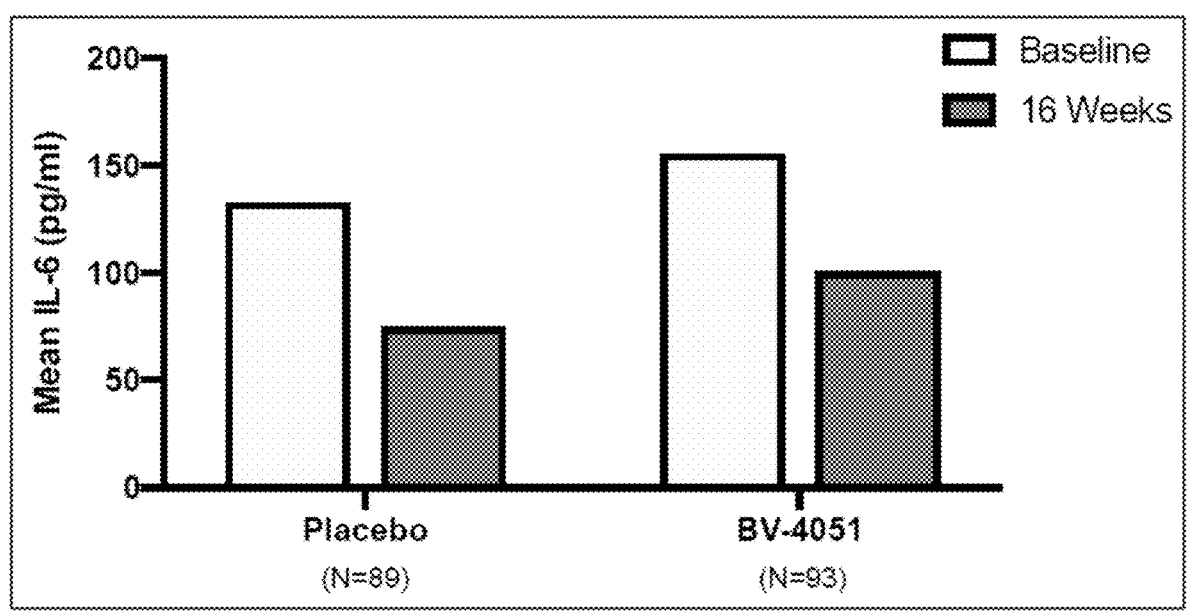
FIG. 2 is a diagram of Interleukin-6 level, measured as a readout direct indicator of disease-modifying activity.

In FIG. 2, Interleukin-6 level was measured as a readout direct indicator of disease-modifying activity. At the end of the 16 weeks of the initial double-blind phase of the study, BV-4051 demonstrated a very positive trend.

Figure 3:
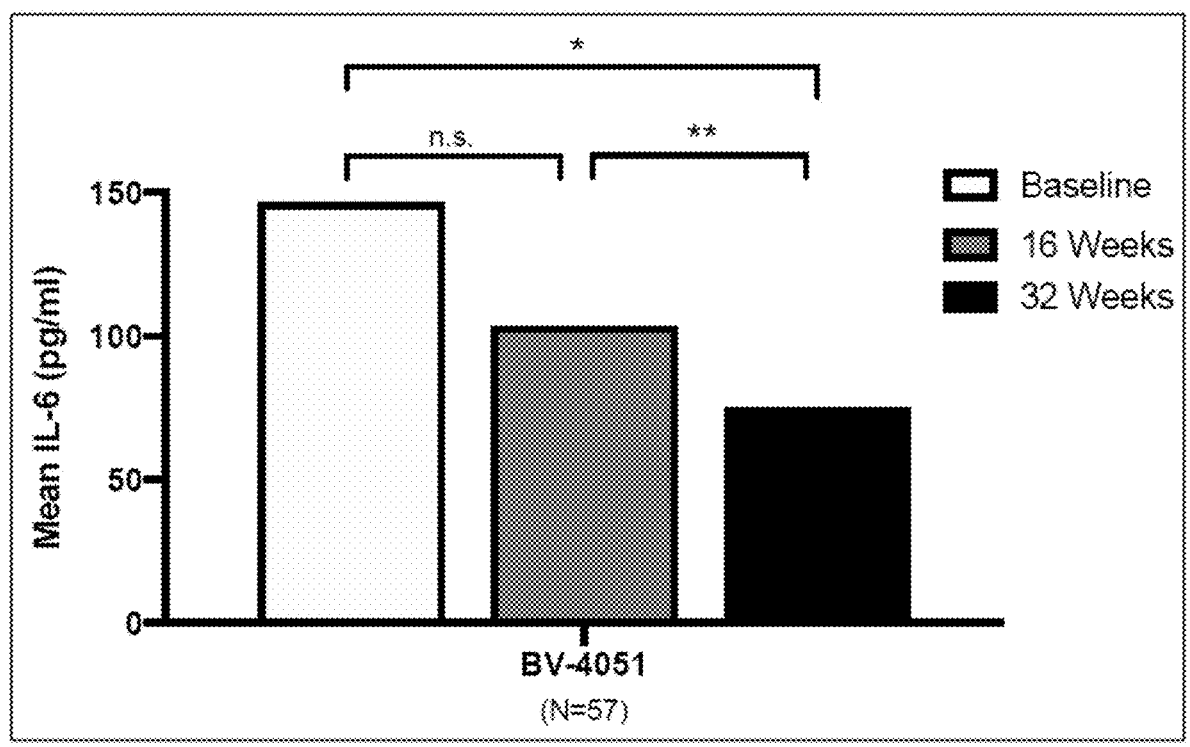
FIG. 3 is a diagram of the Interleukin-6 levels of FIG. 2, at 32 weeks.

In FIG. 3, on further continuation to 32 weeks, IL-6 was statistically significant at a p value 0.03*. Further, the IL-6 levels at 32 weeks in comparison with the baseline was a highly statistically significant p<0.005** (Wilcoxon Signed Rank test).

BV-4051 Lowers Rheumatoid Factor (RF)—RA Study

Rheumatoid factors (RF) are proteins produced by the immune system that can attack healthy tissue in the body. Increased levels of rheumatoid factor in the blood are most often associated with autoimmune diseases, such as rheumatoid arthritis and others. Effect on RF is a direct indicator of therapeutic remission in the progression of rheumatoid arthritis.

Figure 4:
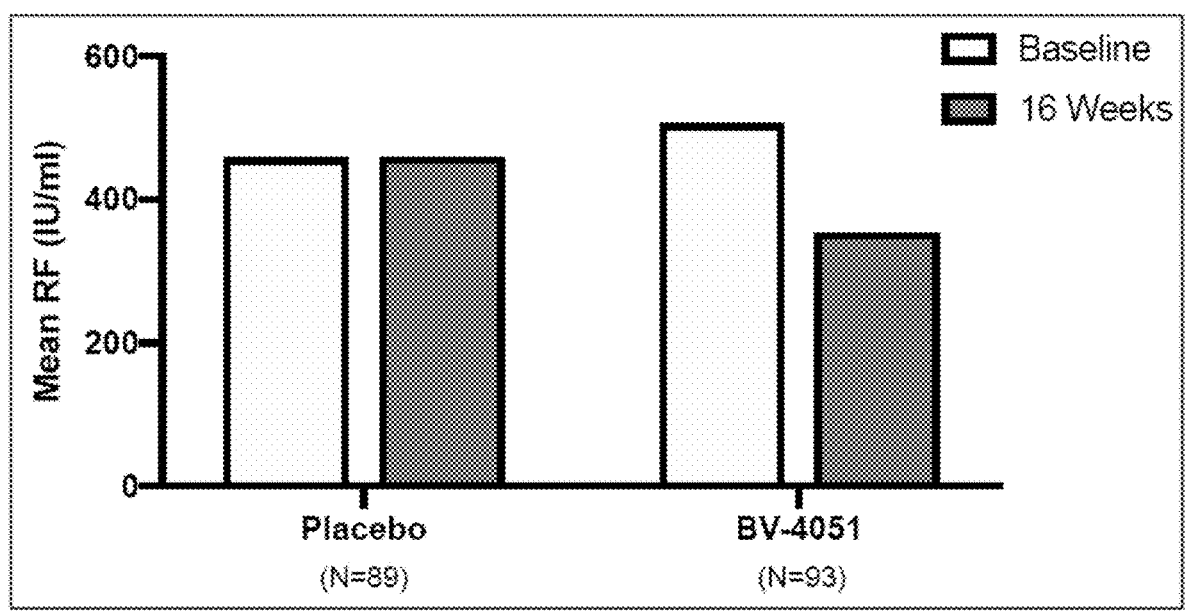
FIG. 4 is a diagram of decrease of rheumatoid factor (RF) titer at 16 weeks, during treatment of rheumatoid arthritis with an example BV-4051 formulation.

In FIG. 4, at the end of 16 weeks, it was observed that an example formulation of BV-4051 caused a decrease in the RF titer. This reduction was statistically significant (p value <0.05 by Mann Whitney's Rank Sum test) in relation to the placebo group.

BV-4051 Lowers ESR and CRP—RA Study

A high Erythrocyte Sedimentation Rate (ESR) or a high level of C-reactive protein (CRP) in the blood are markers of ongoing inflammation. This can be caused by a wide variety of conditions, ranging from infection to cancer. High CRP levels can also indicate that there is inflammation in the arteries of the heart, which can mean a higher risk of heart attacks or myocardial infarcts.

Figure 5:
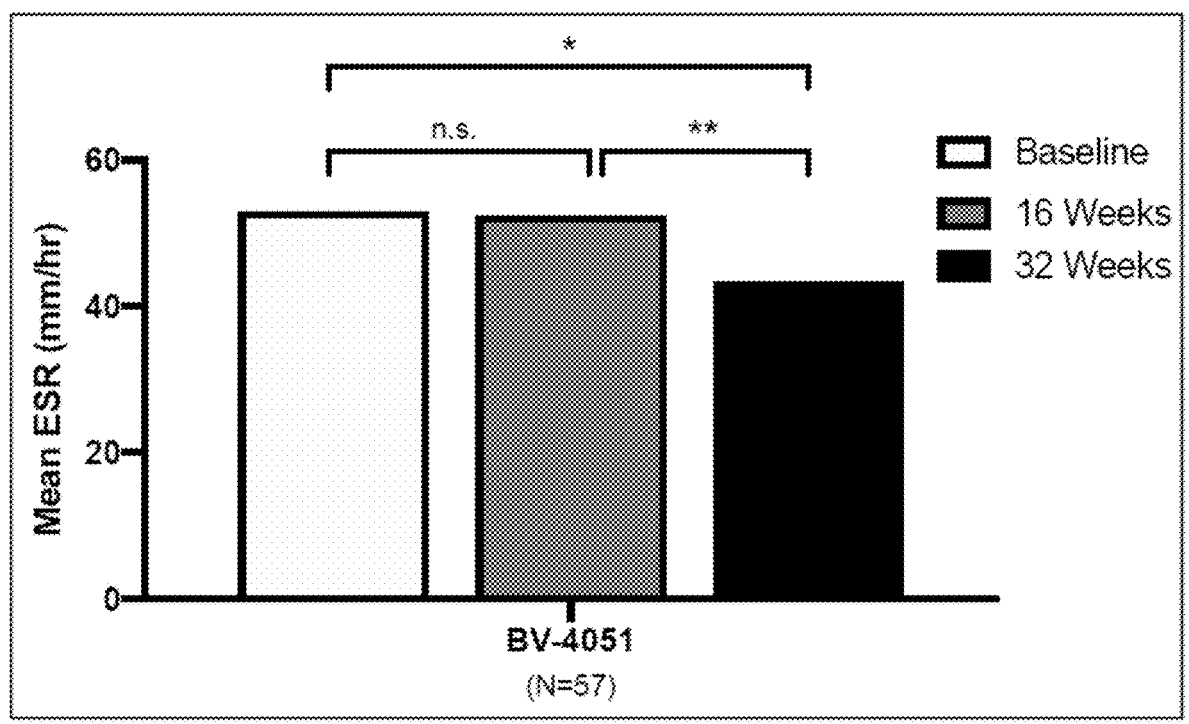
FIGS. 5-6 are diagrams of reduced ESR and CRP levels at 16 weeks, during treatment of rheumatoid arthritis with an example BV-4051 formulation.
Figure 6:
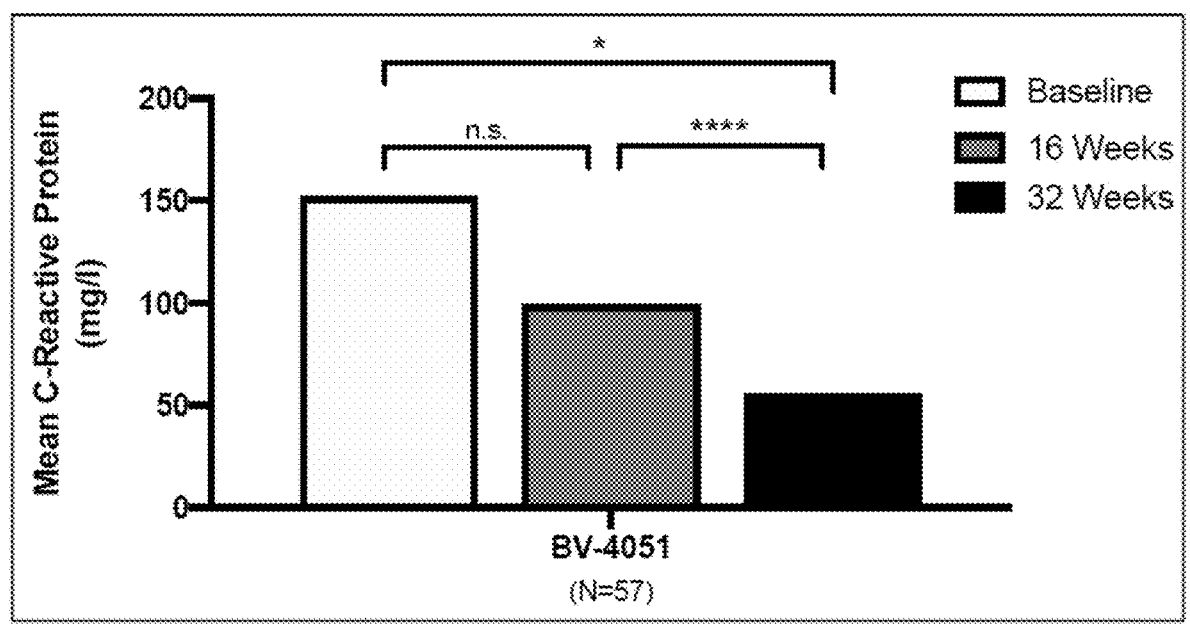

In FIGS. 5-6, treatment with an example formulation of BV-4051 for 16 weeks trended towards reduced ESR and CRP levels. This reduction was statistically significant after 32 weeks of cumulative therapy with the regimen. The changes in these two parameters on a continuous assessment are shown in FIGS. 5 and 6 respectively.

BV-4051 Lowers TNF-α from Lipopolysaccharide (LPS) Induced Macrophages

Figure 7:
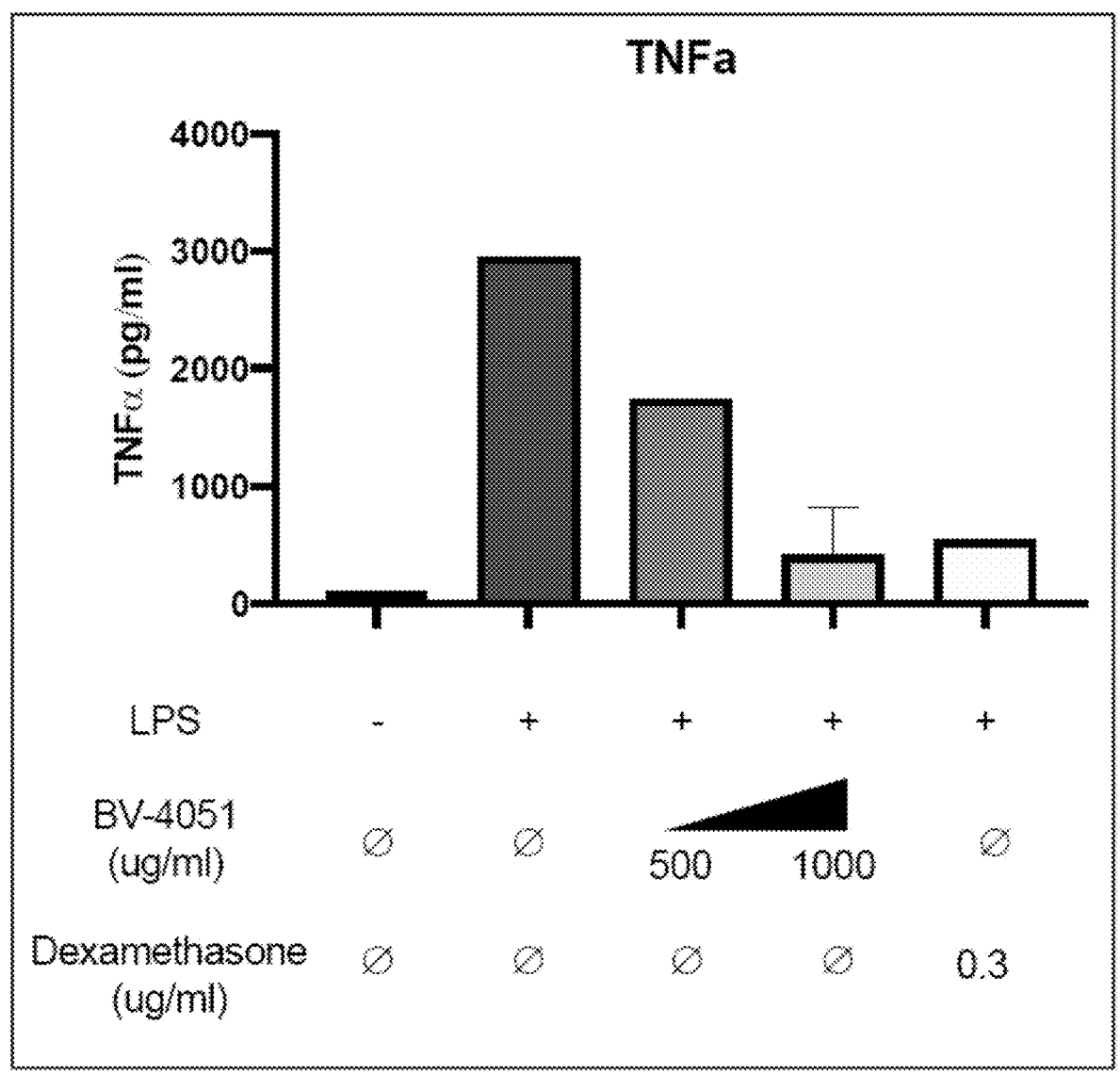
FIG. 7 is a diagram of lowered TNF-α levels from lipopolysaccharide (LPS) induced macrophages, during administration of an example BV-4051 formulation.

Referring to FIG. 7, a mouse macrophage cell line (RAW 267.7) was stimulated with 10 ng/ml LPS to induce inflammatory pathways. Cell supernatants were harvested 24 hours later and TNF-α production was detected using an Enzyme Linked Immunosorbent Assay (ELISA). A dose dependent effect of an example formulation of BV-4051 on reducing TNF-α was observed. At higher doses, the effect was similar to, if not better, than dexamethasone, a corticosteroid that inhibits signaling via the receptor for LPS by blocking the Nuclear Factor kappa B (NF-kB) pathway.

*Withania somnifera* Enhances Cardiorespiratory Function

As further evidence in favor of using formulations of BV-4051 for treatment of COVID-19 disease, one of the main components of the formulation in isolation, *Withania somnifera* or Ashwagandha, can enhance cardiorespiratory function. Cardiovascular health affects the rate at which oxygen can be delivered to the entire body. Readouts for this include maximal cardiac output, pulmonary diffusion, blood volume, and blood flow. Measurement of the maximal aerobic capacity ($VO_2$ max) reflects the ability of the cardiorespiratory system to transport oxygen to the exercising person. After eight weeks of treatment with oral Ashwagandha in a clinical trial, significant improvement in $VO_2$ max was observed relative to the placebo group which demonstrated no change with respect to their baseline parameters. This feature helps the blood oxygen levels during example BV-4051 treatments of COVID-19 patients.

Example BV-4051 formulations, in both solid and liquid dosage forms, reduce COVID-19 symptoms by blocking multiple proinflammatory cytokines such as IL-6 and TNF-α. BV-4051 formulations can decrease the severity of the disease and its clinical manifestation, resulting in reduced morbidity and mortality. Formulations of BV-4051 can also counteract the severe inflammation seen in moderately and severely ill patients with COVID-19. The BV-4051 formulation stabilizes the clotting factors in the body, providing prophylaxis against thromboembolic events. BV-4051 preparations also act against multiple inflammatory pathways including NfkB, p38 MAP kinase, and TBK-1. BV-4051 formulations can stop the propagation of the virus, blocking some commonly used cellular host factors necessary for this virus to continue its lifecycle. Safety of BV-4051 formulations has been established in controlled pre-clinical and clinical studies. Example BV-4051 formulations can be used in adjunct with other agents, such as chloroquine phosphate, hydroxychloroquine, RNA-dependent polymerase (RdRp) inhibitors, remdesivir, interferon-α, lopinavir, ritonavir, ribavirin, favipiravir, and many other agents.

As a treatment or prophylactic, the BV-4051 formulations can also be used alone or in combination with agents such as vitamin C, lysine, zinc, and so forth, for a safe and effective barrier to stimulate the body's defense mechanism and aid against development of COVID-19 disease or related conditions.

Example Process

FIG. 8 shows an example method 800 of neutralizing a Covid-19 disease-specific pro-inflammatory cytokine, in a Covid-19 patient. Operations of the example method 800 are shown in individual blocks.

At block 802, an extract of *Withania somnifera* is obtained from a first hydroglycolic extraction process.

At block 804, an extract of *Boswellia serrata* is obtained from a second hydroglycolic extraction process.

At block 806, an extract of *Zingiber officinale* is obtained from a third hydroglycolic extraction process.

At block 808, an extract of *Curcuma longa* is obtained from a fourth hydroglycolic extraction process.

At block 810, the *Withania somnifera, Boswellia serrata, Zingiber officinale*, and *Curcuma longa* are mixed into a compound comprising, by weight, approximately 5.00 parts of the *Withania somnifera*, approximately 5.00 parts of the *Boswellia serrata*, approximately 1.33 parts of the *Zingiber officinale*, and approximately 1.00 parts of the *Curcuma longa*.

At block 812, the compound is administered to a COVID-19 disease patient.

Phase III Clinical Trial

A multi-center, randomized, double-blind, placebo-controlled Phase III clinical study was conducted to assess the safety and efficacy of example BV-4051 formulated tablets combined with the Current Standard of Care, and the impact of the example BV-4051 on inflammatory biomarkers in subjects with uncomplicated moderate SARS-CoV-2 infections (COVID-19), from September 2020 to April 2021.

The study was performed in compliance with protocol, International Conference on Harmonization (ICH), and all applicable Good Clinical Practices (GCP) and regulations. All required study documentation is archived as required by regulatory authorities. The study was managed by Klinera Global Services, a global clinical research organization based in San Jose, Calif. The protocol was filed with Drugs Controller General of India on Aug. 31, 2020 and amended on Sep. 16, 2021. The protocol was also filed with Department of Ayush, Government of India on the same date Aug. 31, 2020 and amended on Sep. 16, 2021. The study is registered in Clinical Trials Registry of India with details as follows: http://ctri.nic.in/Clinicaltrials/showallp.php?mid1=46041&EncHid=&userName=BV-4051 CTRI/2020/09/027817 [Registered on: Sep. 15, 2020]

Synopsis of the BV-4051 Clinical Study Protocol—Drug Code: BV-4051

Title: A Multi-center, Randomized, Double-Blind, Placebo-Controlled Phase III Clinical Study to assess the Safety and Efficacy of BV-4051 Tablets combined with the Current Standard of Care and its impact on Inflammatory Biomarkers in Subjects with Uncomplicated Moderate SARS-CoV-2 infections (COVID-19).

Study Centers: 4 study centers, competitive enrollment method.

Phase of Clinical Development: Phase III

Population:

Inclusion Criteria:

1. Male, Female
2. 18 to 65 years
3. Subjects with acute uncomplicated moderate Coronavirus infections needing hospitalization with temperature ≥38° C. (100.4° F.); plus at least one respiratory symptom (nasal congestion, sore throat, cough, breathing difficulty {Respiratory Rate≥24 breaths per minute or oxygen saturation ($SpO_2$) <94% on room air}); and at least one constitutional symptom (aches or pains, fatigue, headache, chills or sweats). If antipyretics were taken, subjects were asked to wait at least 4 hours after dosing of the antipyretic to determine if a qualifying temperature was observed.
4. Subjects with laboratory confirmed SARS-CoV-2 infection (COVID-19) as determined by the Reverse Transcription Polymerase Chain Reaction (RT-PCR) or other approved commercially available or public health assay prior to Visit 1.
5. Onset of symptoms at least 48 hours but no more than 96 hours before Visit 1 (Screening; study drug administration visit). The onset of symptoms is defined as either:
   a. Time of the first increase in body temperature to ≥38° C. (100.4° F.); or
   b. Time when the subject experienced at least one general or respiratory symptom.
6. Subjects who were able to understand and willing to sign the informed consent form (ICF).
7. Subjects who were willing and able to comply with all scheduled visits, treatment plans, laboratory tests, lifestyle considerations and other study procedures.
8. All female subjects of child-bearing potential had to document a negative urine pregnancy test result. All female subjects of child-bearing potential and male subjects and their spouse/partner agreed to use a medically acceptable method of contraception (e.g., abstinence, an intrauterine device, a double barrier method such as condom+spermicidal or condom+diaphragm with spermicidal, a contraceptive implant, an oral contraceptive or have a vasectomized partner with confirmed azoospermia) throughout the entire study period, and for 30 days for females and 90 days for males after study drug discontinuation.

Exclusion Criteria:

1. Subjects with severe COVID-19 infection requiring intensive inpatient treatment.
2. Subjects requiring mechanical ventilation or ECMO at the time of randomization on Day 1.
3. Subjects with severe symptoms such as respiratory rate >30 breaths per minute or oxygen saturation ($SpO_2$) <90% on room air.
4. Subjects with other concurrent infections requiring systemic antiviral therapy prior to screening.
5. Administration of immunomodulators, interferon inducers, homeopathic, hormonal other than hormone replacement therapy, and antiviral drugs during the previous 4 weeks before the first dose. Use of corticosteroids as part of the current standard of care is permitted.
6. Subjects who had any of the following documented conditions: uncontrolled hypertension (systolic blood pressure >140 mm Hg or diastolic blood pressure >90 mm Hg), diabetes, asthma (any current or recent, not childhood if resolved), COPD (any), cardiac, hepatic, renal (including eGFR<60) and hematopoietic disorders, bleeding tendency or hemorrhagic disease, neurological system disease, compromised immune system (including patients receiving immunosuppressant therapy, or those with cancer within the past 5 years or human immunodeficiency virus [HIV] infection), endocrine disorders (including thyroid disorders).
7. Subjects with anatomical nasal obstruction or gross anatomical abnormalities. For example, nasal polyps or significant nasal septal deviation.
8. Clinically obese subjects with BMI≥40.
9. Subjects with recent history (within 6 months) of alcoholism or substance abuse.
10. Participation in other clinical trial within 1 month, or during the study.
11. Pregnant or breast-feeding female subjects
12. Allergy or known allergy to components of study medication.
13. Previous history of difficulty swallowing capsules or tablets.
14. Any other associated disease or condition which, in the opinion of the investigator, may have restricted or impeded participation in the study or affect the study results.

Efficacy Parameters:

Primary parameters: To investigate the improvement in reducing the duration and severity of illness compared to placebo.

Where duration of illness is defined as: the length of time to alleviation of all symptoms including fever, nasal congestion, sore throat, cough, breathing difficulty, aches and pains, fatigue, headache, chills/sweats, diarrhea, vomiting, smell disorders, and taste disorders.

The duration of alleviation was calculated from time 0 (first administration of study medication) to the time at which symptom was alleviated.

Alleviation of fever: oral temperature is lower than 37.3° C. (99.10° F.) and stable for at least 24 hours.

Alleviation of other symptoms: The symptom was less than or equal to mild (score is 1 or 0) and stable for at least 24 hours.

Secondary Parameters:

1. The reduction in duration of alleviation of individual symptom: from time 0 (first administration of study medication) to the time at which the symptom was less than or equal to mild and stable for at least 24 hours.

2. The reduction of duration of alleviation of fever: from time 0 (first administration of study medication) to the time at which oral temperature was lower than 37.3° C. (99.10° F.).

3. The percentage of subjects experiencing alleviation of COVID-19 symptoms at every 24 hours post first dose to the end of day 14.

4. The percentage of subjects that experienced complications.

5. The average of severity scores every 24 hours post first dose to the end of day 14.

6. Quality of Life assessment based on the self-assessment questionnaire.

7. Hospitalization rate of subjects with severe COVID-19 symptoms requiring intensive inpatient treatment.

Exploratory Parameters:

1. Duration of viral shedding: defined as the time from treatment initiation to the time of first negative COVID-19 virus RNA by quantitative RT-PCR and/or to the time of first negative COVID-19 virus test result using other approved commercially available or public health diagnostic assay.

2. Reduction in viral shedding from baseline to the subject discharge day from the hospital post treatment initiation.

3. Improvement in pro-inflammatory biomarkers namely, lactate dehydrogenase (LDH). C-Reactive Protein (CRP), Interleukin-6 (IL-6), Tumor Necrosis Factor (TNF), and Erythrocyte Sedimentation Rate (ESR).

Safety Parameters:

Safety was assessed by monitoring and recording all AEs and serious adverse events (SAEs); regular monitoring of complete blood count, clinical chemistry, and urinalysis; results of physical examinations, regular measurement of vital signs, and Electrocardiogram (EKG).

Concomitant Medications:

Any other medications used in the treatment of COVID-19 or related symptoms other than allowed by the Current Standard of Care were not permitted by the protocol during the study; including but not limited to antiviral drug, hormonal drugs, antipyretic and analgesic drugs, and any herbal medicines or supplements.

Withdrawal Criteria

Decision from Investigator

1. Complications or physiological abnormalities that could make the subject, in the opinion of investigator, ineligible for participating in this study.

2. Subject received less than 80% or more than 120% of study medication.

3. Subject with severe adverse event(s), in the opinion of investigator, for safety reasons would be required to withdraw from the BV-4051 study.

4. Subject who used medications that are prohibited by the protocol.

5. Subject stopped taking study medication or refused to comply with study visits, treatment plans, laboratory tests, lifestyle considerations and other study procedures.

6. In the unlikely event of a study participant becoming severe and requiring intensive inpatient treatment; taking the oral investigational product may be difficult. Therefore, the subject would be withdrawn from the study; however, their progress till their hospital discharge would be documented.

Decision from Subject

The participation in the study was voluntary and Subjects were allowed to withdraw from the study at any time with or without any reason(s).

The study medication, in all withdrawn cases, was returned to the site in the original package within 48 hours of completing or stopping the participation in the trial.

Statistical Analysis

Demographics, disposition and baseline characteristics were tabulated by treatment assignment.

Descriptive statistics (n, mean, standard deviation [SD], median, minimum and maximum) were provided for all the continuous variables. Frequency count (n) and percentage (%) of patients were provided for the categorical variables.

All efficacy and safety endpoints were analyzed using ANOVA/ANCOVA for continuous data and using chi-square test for categorical data.

Adverse drug reactions were statistically described. An $\chi^2$ test and Fisher's exact test were used for comparisons of incidence rate of adverse events between groups. Descriptive statistics for laboratory test results were compared between the two treatment groups. Changes from baseline of lab test results before and after treatment were compared between the two treatment groups if necessary.

All statistical tests were conducted at the 5% significance level unless otherwise indicated.

Results

The multi-center study was conducted at 4 hospital sites in the Western State of Maharashtra, in India. This State has had the most COVID-19 disease cases since the start of the pandemic, more than 3 times those of the #2 State. In addition, this State has had the most COVID-19 deaths, more than 4 times those of the #2 State in deaths. This shows the severity of the illness in the study subject population. Each of the sites was a COVID-19 treatment multi-specialty hospital, having all ultra modern diagnostics, as well as full intensive care and cardiac care units for treatment of moderate to severe COVID-19 patients and handling all possible complications of the disease. The Principal Investigators and clinical trial personnel were highly trained and experienced at conducting rigorous clinical studies in the past.

82 subjects were recruited and completed the study during the first wave of the pandemic from late September 2020 to Feb. 15, 2021. 94 subjects were recruited and completed the study during the second wave from Feb. 15, 2021 to Apr. 3, 2021. The second wave is due to a double mutant virus variant namely B.1.617. This variant is reported to have developed from other variants in California and South Africa.

Sample Size

1. A Total of 215 subjects with moderate COVID-19 were screened for inclusion in this trial. Of that, 206 subjects were randomized of which 176 subjects completed the study of 14 days duration.

2. All randomized subjects were assigned to one of the two arms according to the randomization scheme on Day 1 in the ratio of 1:1.

a) Arm A: BV-4051 tablets+Current Standard of Care, 89 subjects.

b) Arm B: Placebo tablets+Current Standard of Care, 87 subjects.

The subject visits were concluded on Apr. 3, 2021. The full scope of analytical work and biostatistics took several weeks to complete. The demographics were well matched between the Active and Placebo groups. There were no significant adverse events reported in the active subjects. There was no worsening of signs and symptoms in the active group and no deaths during the study duration. An interim analysis was conducted for Primary Efficacy-Reduction of duration of illness. The BV-4051 formulation achieved statistical significance in alleviation of all symptoms, in the Intent to Treat analysis with p=0.038, as well as Per Protocol analysis with p=0.027.

The two most commonly used non-vaccine drugs in the treatment of COVID-19 are Remdesivir and Tocilizumab. The first study using Remdesivir in 237 subjects reported by Wang and colleagues and completed in May 2020 showed no significant effect. The second study conducted by the National Institutes of Health (ACTT-1) study in 1063 subjects shows an advantage of discharge at 11 days on Remdesivir vs. 15 days on Placebo. A more extensive study as reported by Spinner and colleagues done in 105 hospitals in the US, Europe, and Asia in 584 subjects showed no difference in Active (N=193) vs. Placebo (N=200) in Primary and Secondary End Point Analysis.

The Tocilizumab drug failed to show efficacy for preventing intubation or death in a study of 243 subjects. It further has not shown any definitive efficacy in management of the COVID-19 disease.

The example BV-4051 formulation, also dubbed Artovid-20, showed statistical significance in efficacy even during a second wave of COVID-19 infections, which was due to a double mutant variant of the SARS-CoV-2 virus. This BV-4051 formulation may have additional advantage in the prophylaxis and treatment of the mutant strains of the SARS-CoV-2 virus.

Data Tables of the Clinical Trial

FIG. 9 shows subject disposition for the Phase III Clinical Trial entitled, "Multi-center, Randomized, Double-Blind, Placebo-Controlled Phase III Clinical Study to assess the Safety and Efficacy of BV-4051 Tablets combined with the Current Standard of Care and its impact on Inflammatory Biomarkers in Subjects with Uncomplicated Moderate SARS-CoV-2 infections (COVID-19)."

FIG. 10 shows demographic characteristics for the Phase III Clinical Trial entitled, "Multi-center, Randomized, Double-Blind, Placebo-Controlled Phase III Clinical Study to assess the Safety and Efficacy of BV-4051 Tablets combined with the Current Standard of Care and its impact on Inflammatory Biomarkers in Subjects with Uncomplicated Moderate SARS-CoV-2 infections (COVID-19)."

FIG. 11 shows a primary efficacy analysis, ITTI Population, for the Phase III Clinical Trial entitled, "Multi-center, Randomized, Double-Blind, Placebo-Controlled Phase III Clinical Study to assess the Safety and Efficacy of BV-4051 Tablets combined with the Current Standard of Care and its impact on Inflammatory Biomarkers in Subjects with Uncomplicated Moderate SARS-CoV-2 infections (COVID-19)."

FIG. 12 shows a primary efficacy analysis, PP Population, for the Phase III Clinical Trial entitled, "Multi-center, Randomized, Double-Blind, Placebo-Controlled Phase III Clinical Study to assess the Safety and Efficacy of BV-4051 Tablets combined with the Current Standard of Care and its impact on Inflammatory Biomarkers in Subjects with Uncomplicated Moderate SARS-CoV-2 infections (COVID-19)."

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of the present invention. The benefits, advantages, solutions to problems, and any element(s) that may cause any benefit, advantage, or solution to occur or become more pronounced are not to be construed as a critical, required, or essential features or elements of any or all the claims. The present invention is defined solely by the appended claims including any amendments made during the pendency of this application and all equivalents of those claims as issued.

The invention claimed is:

1. A method for treating effects of COVID-19 disease in a patient, comprising:

obtaining an ashwagandha (*Withania somnifera*) extract from a first instance of a hydroglycolic extraction process applied to an ashwagandha plant;

obtaining a shallaki (*Boswellia serrata*) extract from a second instance of the hydroglycolic extraction process applied to a shallaki plant;

obtaining a ginger (*Zingiber officinale*) extract from a third instance of the hydroglycolic extraction process applied to a ginger plant;

obtaining a turmeric extract (*Curcuma longa*) from a fourth instance of the hydroglycolic extraction process applied to a turmeric plant;

wherein each instance of the hydroglycolic extraction process for obtaining a respective extract comprises soaking a respective plant material in chloroform and aqueous 60% methanol for 8-12 hours;

filtering the chloroform and aqueous 60% methanol to obtain a first residue and a first filtrate;

settling the first filtrate to provide two immiscible layers, wherein the two immiscible layers are an aqueous methanol layer and a chloroform layer;

separating the chloroform layer;

concentrating the chloroform layer to obtain a first dry extract of the respective plant material;

dissolving the first dry extract in hexane;

filtering the first dry extract dissolved in the hexane to obtain a second residue and second filtrate;

drying the second residue and storing the second residue as a first fraction;

re-extracting the first fraction with the hydroglycolic extraction process to obtain a second fraction;

combining the first and second fractions to provide a pharmacologically active fraction of the respective plant material;

mixing the pharmacologically active fraction of the ashwagandha extract, the pharmacologically active fraction of the shallaki extract, the pharmacologically active fraction of the ginger extract, and the pharmacologically active fraction of the turmeric extract into a compound comprising, by weight, 5 parts of the pharmacologically active fraction of the ashwagandha extract by weight, 5 parts of the pharmacologically active fraction of the shallaki extract by weight, 4/3 parts of the pharmacologically active fraction of the ginger extract by weight, and 1 part of the pharmacologically active fraction of the turmeric extract by weight; and orally administering between 500-3600 milligrams of the compound per day to the patient.

2. The method of claim 1, further comprising mixing the pharmacologically active fraction of the ashwagandha extract, the pharmacologically active fraction of the shallaki extract, the pharmacologically active fraction of the ginger extract, and the pharmacologically active fraction of the turmeric extract with a liquid vehicle for oral administration as a liquid preparation.

3. The method of claim 1, further comprising mixing to make the compound in proportions of:
- 270 mg of the pharmacologically active fraction of the ashwagandha extract;
- 270 mg of the pharmacologically active fraction of the shallaki extract;
- 72 mg of the pharmacologically active fraction of the ginger extract;
- 54 mg of the pharmacologically active fraction of the turmeric extract;
- 1 ml propylene glycol; and
- 8.5 ml purified water.

4. The method of claim 2, further comprising administering the compound in a liquid oral dose, for administration 4 times per day (QID) to the patient.

5. The method of claim 1, wherein the step of dissolving the first dry extract in hexane further comprises de-pigmenting, de-fatting, or detoxifying the first dry extract dissolved in the hexane.

6. The method of claim 1, further comprising orally administering the compound to the patient for 11-14 days.

7. The method of claim 1, wherein the mixing the pharmacologically active fraction of the ashwagandha extract, the pharmacologically active fraction of the shallaki extract, the pharmacologically active fraction of the ginger extract, and the pharmacologically active fraction of the turmeric extract into the compound further comprises:
- mixing 10.6 kg of the pharmacologically active fraction of the ginger extract with 3.96 kg of the pharmacologically active fraction of the turmeric extract to make a first component;
- mixing 29 kg of the pharmacologically active fraction of the shallaki extract with 39.6 kg of the pharmacologically active fraction of the *Withania* extract to make a second component, and sifting the second component though a #30 mesh;
- mixing 3.96 kg of the pharmacologically active fraction of the turmeric extract with 10.6 kg of the pharmacologically active fraction of the shallaki extract to make a third component;
- blending the first component, the second component, and the third component together in a blending rapid mixer for 10 minutes to make a granulated mixture; and
- passing the granulated mixture through a #16 mesh.

8. The method of claim 7, further comprising, before blending the first component, the second component, and the third component together in the blending rapid mixer:
- mixing the first component with 5.11 kg of starch, 3.1 kg of powdered silica, and 2.6 kg of polacrilin potassium;
- mixing the second component with 16.45 kg of the starch, 3.8 kg of the powdered silica, 6.6 kg of the polacrilin potassium, and 20 liters of isopropyl alcohol; and
- mixing the third component with 2.6 kg of the powdered silica, 2.2 kg of micro-cellulose, 1.2 kg of SLS, 2.6 kg of the polacrilin potassium, and 20 liters of the isopropyl alcohol.

9. The method of claim 7, further comprising at least compressing the granulated mixture received from the #16 mesh into approximately 220,000 tablets for oral administration;
- core coating the approximately 220,000 tablets; and
- film coating the approximately 220,000 tablets.

* * * * *